(12) United States Patent
el Kaliouby et al.

(10) Patent No.: US 10,111,611 B2
(45) Date of Patent: Oct. 30, 2018

(54) PERSONAL EMOTIONAL PROFILE GENERATION

(71) Applicant: Affectiva, Inc., Waltham, MA (US)

(72) Inventors: Rana el Kaliouby, Boston, MA (US); Avril England, Pleasanton, CA (US)

(73) Assignee: Affectiva, Inc., Boston, MA (US)

( * ) Notice: Subject to any disclaimer, the term of this patent is extended or adjusted under 35 U.S.C. 154(b) by 62 days.

(21) Appl. No.: 14/328,554

(22) Filed: Jul. 10, 2014

(65) Prior Publication Data

US 2014/0323817 A1 Oct. 30, 2014

Related U.S. Application Data

(63) Continuation-in-part of application No. 13/153,745, filed on Jun. 6, 2011.
(Continued)

(51) Int. Cl.
*G06K 9/00* (2006.01)
*A61B 5/16* (2006.01)
(Continued)

(52) U.S. Cl.
CPC .......... *A61B 5/165* (2013.01); *G06F 19/3418* (2013.01); *G06F 19/3481* (2013.01); *G06Q 30/0271* (2013.01); *G06Q 30/0282* (2013.01); *G06Q 50/01* (2013.01); *A61B 5/02055* (2013.01); *A61B 5/02405* (2013.01);
(Continued)

(58) Field of Classification Search
CPC .......... G06K 9/00275; G06K 9/00281; G06K 9/0028; G06K 9/00295; G06K 9/00302; G06K 9/00308; G06K 9/00315; G06K 9/00335; G06K 9/00342; G06K 9/00348;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

The mental state of an individual is obtained in order to generate an emotional profile for the individual. The individual's mental state is derived from an analysis of the individual's facial and physiological information. The emotional profile of other individuals is correlated to the first individual for comparison. Various categories of emotional profiles are defined based upon the correlation. The emotional profile of the individual or group of individuals is rendered for display, used to provide feedback and to recommend activities for the individual, or provide information about the individual.

38 Claims, 8 Drawing Sheets

Related U.S. Application Data

(60) Provisional application No. 61/844,478, filed on Jul. 10, 2013, provisional application No. 61/916,190, filed on Dec. 14, 2013, provisional application No. 61/924,252, filed on Jan. 7, 2014, provisional application No. 61/927,481, filed on Jan. 15, 2014, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011.

(51) Int. Cl.

| | | |
|---|---|---|
| *G06F 19/00* | (2018.01) | |
| *G06Q 30/02* | (2012.01) | |
| *G06Q 50/00* | (2012.01) | |
| *A61B 5/0205* | (2006.01) | |
| *A61B 5/024* | (2006.01) | |
| *A61B 5/053* | (2006.01) | |
| *A61B 5/08* | (2006.01) | |
| *A61B 5/11* | (2006.01) | |
| *A61B 5/00* | (2006.01) | |

(52) U.S. Cl.
CPC ............... *A61B 5/0533* (2013.01); *A61B 5/08* (2013.01); *A61B 5/11* (2013.01); *A61B 5/6824* (2013.01)

(58) Field of Classification Search
CPC ........... G06K 9/00355; G06K 9/00362; G06K 9/00241
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | MacLean |
| 5,507,291 A | 4/1996 | Stirbl et al. |
| 5,572,596 A | 11/1996 | Wildes |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dyer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 * | 4/2011 | Sharma ............ G06Q 20/3674 705/14.49 |
| 8,010,458 B2 | 8/2011 | Galbreath et al. |
| 8,401,248 B1 | 3/2013 | Moon et al. |
| 8,487,772 B1 * | 7/2013 | Higgins ............ G06Q 30/0201 340/146.2 |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |

(56) References Cited

U.S. PATENT DOCUMENTS

| | | |
|---|---|---|
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2005/0187437 A1* | 8/2005 | Matsugu ............... A61B 5/16 600/301 |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1* | 11/2007 | de Lemos ............. A61B 3/113 600/300 |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2011/0092780 A1 | 4/2011 | Zhang et al. |
| 2011/0126226 A1 | 5/2011 | Makhlouf |
| 2011/0134026 A1 | 6/2011 | Kang et al. |
| 2011/0143728 A1* | 6/2011 | Holopainen ....... G06K 9/00308 455/414.1 |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0293548 A1 | 11/2012 | Perez et al. |
| 2012/0304206 A1 | 11/2012 | Roberts et al. |
| 2012/0324491 A1 | 12/2012 | Bathiche et al. |
| 2013/0023337 A1 | 1/2013 | Bowers et al. |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Abiol, Alberto, et al. "Face recognition using HOG-EBGM." Pattern Recognition Letters 29.10 (2008): 1537-1541.

* cited by examiner

FIG. 7 an example bar graph with mental states

PERSONAL EMOTIONAL PROFILE GENERATION

RELATED APPLICATIONS

This application claims the benefit of U.S. provisional patent applications "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to generating an emotional profile based upon analysis of mental states.

BACKGROUND

An individual's emotions are an important component of who they are. A person's response to stimuli can have a profound impact on the mental states they experience. The mental state of an individual can run a broad gamut from happiness to sadness, from contentedness to worry, and from excited to calm. These mental states are experienced in response to everyday events such as frustration during a traffic jam, boredom while standing in line, and impatience while waiting for a cup of coffee.

Individuals who are able to understand their emotional states have the option to use the information to accommodate their current abilities or limitations. Many mental states, such as frustration, confusion, disappointment, boredom, disgust, and delight, can be identified and related to behavioral patterns. When confronted with unpleasant mental states, individuals can respond with cravings for pleasure, comfort, reward, or enjoyment. On perhaps an even more visible scale, individuals can often be observed evidencing a collective emotional response, such as responding with fear and anxiety after witnessing a catastrophe or responding with happy enthusiasm when their sports team obtains a victory. When an individual is aware of his or her mental states, he or she is better equipped to realize his or her own abilities, cope with the normal stresses of life, work productively and fruitfully, and make a contribution to his or her community.

SUMMARY

Analysis of mental states can be performed to develop a mental state profile for an individual or group of individuals. The mental states can include emotional states, cognitive states, and/or physiological states. Example mental states include frustration, concentration, confusion, disappointment, hesitation, cognitive overload, focusing, engagement, attention, boredom, exploration, confidence, trust, delight, disgust, skepticism, doubt, satisfaction, excitement, laughter, calmness, stress, happiness, sadness, smiling, frowning, curiosity, and numerous others. Mental state profile information can be used to display patterns and norms for the individual or a group, and can aid in understanding consumer behavior, tailoring products to closer match a user's desires, and improving websites and interfaces to computer programs. A computer implemented method for mental state analysis is disclosed comprising: obtaining mental state data from an individual; analyzing the mental state data to produce mental state information; correlating the mental state information of the individual with mental state information from a plurality of people; and categorizing the individual with others from the plurality of people based on the correlating.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
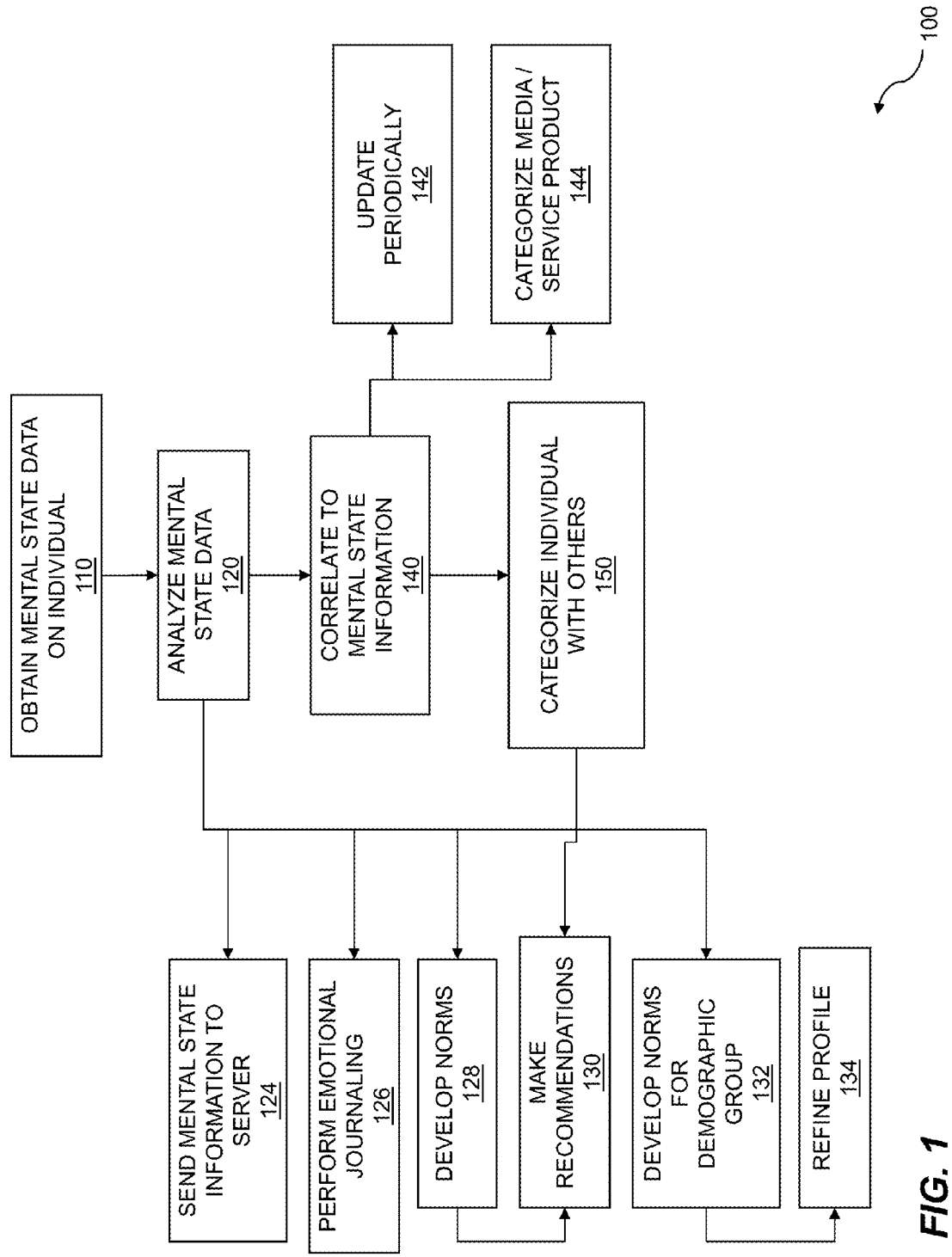
FIG. 1 is a flow diagram for personal emotional profiling.

People exhibit and communicate a wide range of emotions in their daily lives. These emotional states are experienced in response to everyday events and, when identified as a pattern, can create an emotional identity associated with a particular person or group of people. Changes in the emotional state of an individual can occur quickly and might not be easily recognized by the individual, often resulting in situations where the individual has difficulty summarizing and describing his or her emotional state. Providing an assessment of an emotional state can assist the individual with decision-making, activity selection, activity scheduling, and other tasks. When the assessment describes an emotional characteristic or pattern, the data can allow useful analysis and tailoring of material for the person or group of people.

To this end, a personal emotional profile, which includes a summary or analysis of data representing a person's distinctive features or characteristics, can be created. These characteristics can include the emotional state of an individual at a moment in time or over a period of time. The profile can include distinctive habits, attitudes, qualities, behaviors, and emotional traits of an individual or groups of individuals. The profile can provide the individual, or group of individuals, with perspective and insight about their general emotional characteristics, or their emotional state in response to certain activities or behaviors. In addition, the profile can be used to track reactions of a person or people to certain stimuli. For instance, in a certain embodiment, a profile identifies the number of times that a person has laughed during a certain time period, providing a way to track the responsiveness of the person to humor. Such laugh tracking could be used to identify receptiveness to general or specific types of humor, or to provide the individual with information when certain milestones are reached during the day—10,000 laughs, for example. Additionally, emotional response tracking could be used to gauge and analyze readiness to react to emotional scenes in media. In some cases, certain reactions could be incentivized. For example, game points could be earned and stored within a profile based on certain emotional responses. Some examples of such incentivizing could include giving points to the first individual to laugh when exposed to a certain joke, or to the first individual to evidence emotional distress when exposed to a distressing situation. Other types of scoring could likewise be analyzed and recorded as part of the emotional profile.

Analysis of an individual's emotional state can be used to provide feedback to the individual about the status of his or her well-being. The feedback can be used to create a personal emotional profile of the individual. The emotional states of a plurality of individuals can be correlated and compared to a predefined group of individuals. Various attributes can be associated and used to define categories of individuals with similar emotional profiles. The analysis can take place on a computer with which the user is interacting. This profile information can be combined with additional information about the individual, such as demographic information, to create a more comprehensive outline and summary of the emotional state of the individual. A category from an emotional profile can be used to further enhance the demographic profile. The profile can be used to extrapolate behavior, predict future reactions to certain events, or inform a social profile of an individual. This personal emotional profile can be used to make recommendations for different activities, and can include recommendations for activity performance based upon time of day, a period of time during the day, or other calendar-based scheduling. The profile can also be included in an aggregated analysis along with a plurality of people's emotional profiles allowing for activity recommendations.

A personal emotional profile can be developed by evaluating facial expressions, hand gestures, and physiological conditions exhibited by an individual. For example, the human face is a powerful channel for communicating a wide variety of emotional states. The general expressiveness of an individual as they view input stimuli can be analyzed to determine an emotional state. A camera or another facial recognition device can be used to capture images of an individual's face, and software can be used to extract and interpret laughs, smiles, frowns, and other facial expressions to aid in creating an emotional profile.

Other physiological data can also be useful in determining the personal emotional profile of an individual. Gestures, eye movement, sweating, electrodermal (EDA) activity, heart rate, blood pressure and respiration are a few examples of such potentially useful data sources. A variety of sensor types can be used to capture physiological data, including heart rate monitors, blood pressure monitors, EDA sensors, or other types of sensors. A camera can be useful for simultaneously capturing physiological data and facial images. Sensors coupled to a computer—in some embodiments, the same computer with which the user is interacting; in other embodiments, one or more other computers—can be configured to detect, capture, and/or measure one or more external manifestations of the user's emotional state. For example, a still camera can be configured to capture images of the user's face; a video camera can be configured to capture images of the user's movements; a heart rate monitor can be configured to measure the user's heart rate; a skin resistance sensor can be configured to detect changes in the user's galvanic skin response; and an accelerometer can be configured to measure such movements as gestures, foot tapping, or head tilts, to name a few. In embodiments, multiple sensors to capture the user's emotional state data are included.

Once the data has been collected from the individual, an analysis of the emotional state data is obtained, with the analysis providing insights on the emotional states of the user over time. In some cases, the emotional state of the user can be estimated. Software can be used to extract emotional state information from the physiological data captured in an image or video in order to augment, or replace, the data captured from a camera. In some embodiments, self-report methods of capturing emotional state information, such as the survey approach, are also used in conjunction with emotional state information captured from cameras, sensors, monitors, or other equipment.

Once the emotional state information has been produced, an output can be rendered to the individual. The output can be a quantitative textual personal emotional profile, a graphical representation for the individual, or some other representation. The output can include an analysis of other individuals whose mental state information has been correlated and compared to the profile of an individual. The emotional profile can include data and analysis that is posted on a social network web page. The profile can describe the well-being status of the individual. The profile can also describe recommendations for the individual. The recommendations can include activities such as watching a video, playing a game, or participating in a social activity. The emotional profile can also be used in concert with a calendar where it can be displayed or compared with ongoing activities already included a person's schedule. The process of generating and using an emotional profile can further comprise correlating a profile of an individual to a profile populated with previously established "norms." In embodiments, analysis includes aggregating the profile of the individual with the profiles of a plurality of other people, and correlating the profiles of a plurality of people with activities performed by this plurality. The correlated profiles of a plurality of people can be associated with a category useful in predicting future behaviors or responses.

FIG. 1 is a flow diagram for personal emotional profiling. A flow 100 that describes a computer-implemented method for personal emotional profiling is shown. The flow 100 includes obtaining mental state data on an individual 110. The obtaining can be accomplished by collecting mental state data using sensors, cameras, and other devices. The obtaining can be accomplished by accessing a database and importing mental state data from the database. In some embodiments, the mental state data is already present in a system as a result of previous accessing or data manipulation, and the obtaining simply comprises accessing the already present mental state data. The collecting of mental state data is accomplished using different methods in various embodiments, and can include capturing facial images of an individual as they respond to stimuli. Facial image data can be captured using any type of image-capture device including a webcam, a video camera, a still camera, a thermal imager, a CCD device, a phone camera, a three-dimensional camera, a depth camera, multiple webcams used to show different views of a person, or any other type of image capture apparatus that allows captured data to be used in an electronic system. The general expressiveness and facial changes of an individual as they view input stimuli can be analyzed to determine an emotional state. A camera or another facial recognition device can be used to capture images of an individual's face, and software can be used to extract and interpret laughs, smiles, frowns, and other facial expressions. The obtaining of mental state data can be accomplished while a person observes various types of media including online media content. The obtaining can accomplished by collecting the mental state data over time. In embodiments, the obtaining is accomplished by collecting the mental state with a plurality of devices.

In some embodiments, the data is collected from multiple sources. The collected data can include any type of mental state data including, but not limited to, heart rate, respiration rate, blood pressure, skin resistance, audible sounds, gestures, or any other type of data that can prove useful for determining mental state information. In some embodiments, the mental state data includes electrodermal activity data. The mental state data for an individual can be obtained by analyzing a mental state in light of various other sources of information and generating a mental state profile based upon the mental state data.

The flow 100 can further comprise determining contextual information related to the collected mental state data. Any type of contextual information related to the collection of the mental state data can be obtained. Some examples of contextual information that can be collected include a task assigned to the user, the location of the user, the environmental conditions that the user is exposed to—such as temperature, humidity, and the like—, the name of the content being viewed, the level of noise experienced by the user, or any other type of contextual information. In some embodiments, the contextual information is based on one or more of skin temperature or accelerometer data. In some embodiments, the contextual information is based on one or more of a photograph, an email, a text message, a phone log, or GPS information.

The flow 100 includes analyzing the mental state data 120 to produce mental state information. The analyzing of mental state data 120 can include various types of analysis, including computation of means, modes, standard deviations, or other statistical calculations over time. The analyzing of mental state data 120 can include inferring mental states. The mental state data can include one or more of smiles, laughter, smirks or grimaces. The data sent can include image data, physiological data, and accelerometer data. The mental states which can be determined include happiness, sadness, concentration, and confusion, as well as many other mental states. The categorizing can be based on a plurality of expressions by the individual. The categorizing can further be based on a rate of change in the facial expressions by the individual. In embodiments, the rate of change is evaluated during exposure to specific media. Mental state data can be collected sporadically or continually over a time period to create a profile. The profile can include a summary of the mental state analysis. In some embodiments, the data which is sent to the server is a subset of the data that was captured on the individual. In some embodiments, a subset of the data collected on an individual is analyzed and sent to a server. The analyzing of the mental state data can be accomplished at least in part on a server. The mental state data can pertain to an emotional state, a cognitive state, and/or a physiological state.

The flow 100 continues by sending mental state information to a server device 124. In some embodiments, the mental state information is generated in the form of a description or summary. The information can be sent to the server 124 for further mental profile analysis or for correlation with other people's profiles or analysis. In embodiments, the mental state data is analyzed by the computer with which the user is interacting, the computer or computers that captured the sensor data, and/or one or more other computers that can be local or remote to the user to produce the mental state information. In embodiments, the information sent to the server 124 remains in the form of mental state data. The data sent to the server can comprise various types of mental state data including, but not limited to, facial data, heart rate, respiration rate, blood pressure, skin resistance, skin temperature, accelerometer data, mental state inference, audible sounds, gestures, electrodermal data, and/or contextual data.

The mental state data 120 can augmented through emotional journaling 126. An individual might find that entering a comments in a digital or online journal, using a journaling application, or writing their emotions down on paper can help them to process difficult times as well as help them sort out general emotions. The information provided by the individual as part of their journaling may be included in the analysis used in developing a personal emotional profile.

The flow may comprise developing norms 128 for an individual. Emotional experiences, including contentedness, sadness, worry, joy, fury, fear, or regret, can result from a unique combination of thinking, behavior, and bio-physiological changes which take place in the human body as it experiences a life event. In one sense, emotions can be conceptualized as dependent variables, with experiences serving as independent variables. Individuals who experience similar events can be categorized based on similar or dissimilar response to those events. Valence represents one variable that can aid in such categorization. Valence measures the intrinsic attractiveness (positive valence) or averseness (negative valence) of an event, object, or situation. Emotions with the similar valence (i.e. anger and fear) can result in a similar influence on judgments and choices among a plurality of individuals. Individuals can also exhibit similar emotional experiences based upon demographic criteria including age, education, race, location, and other factors. A variance from a person's expected responses to emotional stimuli can indicate a useful categorical difference that can be used to update an emotional profile. A personal emotional profile can include an analysis of a person's emotional state compared to certain norms. The flow 100 can include developing norms 128 for a plurality of individuals and these norms can be factored into emotional profiling. Activities and analysis can be used to develop norms applicable to a plurality of individuals. The norms established for a group can be based on a correlation of emotional responses from a plurality of individuals. The flow 100 can include the correlation of norms for an individual with the norms established for a group, including a demographic group.

The flow can include making recommendations 130 to the individual based upon their personal emotional profile. This feedback can include recommendations for different activities, and can include recommendations for performing activities based upon time of day, a period of time during the day, or another type of calendar-based scheduling. The flow can further comprise using response differences of the individual, over an interval of time, from the norms for the individual to make a recommendation 130. For example, for an individual whose personal emotional profile correlates with the profiles of other individuals of a similar demographic category, a response to a particular event or circumstance for that individual that is different than the demographic norm can trigger the system to offer a different recommendation than the recommendation provided to the individuals scoring near the norm. The different response recommendations can become part of the individual's emotional profile. Response differences can be evaluated on an hourly, daily, or weekly basis. The recommendations can include activities such as watching a video, playing a game, or participating in a social activity, to name a few. The recommendations derived from the emotional profile can also be included in a calendar where they can be displayed or compared with the ongoing activities already included in the calendar. In some embodiments, an individual's emotional profile is correlated to emotions that occur in response to a particular activity. Additionally, the analysis can include aggregating the emotional profile of the individual with the emotional profile of a plurality of other people, and further correlating the emotional profile of a plurality of people with activities performed by the plurality in order to make a recommendation.

The flow can include developing norms for a demographic group 132. The characteristics of the group can include any demographic, such as age, sex, marital status, literacy/education, employment status and occupation, geographical location, place of birth, language, religion, nationality, ethnicity, race, and citizenship, among others. Individuals who comprise a group defined by one or more of these demographic attributes can potentially experience generally similar emotional responses to an event. In order to further refine the demographics-based classification, typical emotional response can be inferred based upon the aggregate response to an event or life circumstance from a plurality of members of the demographic group. The norm of the demographic, and any variances from the norm of the demographic, can be used to adjust or refine the emotional profile 134 of an individual or the emotional profile of a group. The flow 100 can include using response differences in the individual from the norms for the demographic group to refine a profile 134.

The flow 100 continues with correlating previously determined mental state information of the individual with the mental state information from a plurality of people 140. The correlation includes analysis that can identify complementary relationships based upon similar mental states resulting from similar events or life circumstances. The correlation between an individual and a group of individuals can be based upon data captured during an activity performed by the individual or the group of individuals. The activity can comprise an interaction with a web site, a movie, a movie trailer, a product, a computer game, a video game, a personal game console, a cell phone, a mobile device, an advertisement, or another action such as consuming food. As used herein, interaction refers to both passive viewing and active viewing and responding. The correlation between an individual and a group of individuals can be based upon data related to a demographic profile. Other characteristics of a plurality of individuals can be correlated with the characteristics of an individual to refine an emotional profile.

A media or service-type product can be categorized 144 based upon the emotional response of an individual or plurality of individuals. The categorizing can be part of an emotional profile. The similar response of a plurality of individuals to a media or service product can create a correlation among those individuals, which in turn can be categorized within a profile. The media/service product can include any type of content such as broadcast media, digital media, electronic media, multimedia, news media, print media, published media, recorded media, social media, online media, and other forms of media content. The emotional profile of an individual or plurality of individuals can be determined as the individual or plurality are watching or interacting with the media. Digital media can be categorized based on a profile. For example, some embodiments include a media presentation prepared with different versions, and, depending on the goal of the media presentation, collected emotional profile data can be used to determine which media presentation generated the most positive or negative affect data. Other embodiments use emotional profile information to determine the duration for the media presentation. In still other embodiments, the emotional profile information is used to determine the presentation location of a media presentation. In some embodiments, the media presentation is optimized for a specific platform, such as a mobile phone, tablet computer, or mobile device. Other embodiments optimize the media presentation for a home TV screen, a large movie theater screen, or a personal computer screen, based upon the analysis of an individual's emotional profile as they view various media on different devices. Likewise, the profile can be used to categorize, analyze, or optimize a product or service.

As emotional profile information is collected, the personal emotional profile of an individual is periodically updated 142. The profile can be updated in real time or can be updated at the conclusion of an event. The profile can be updated periodically, such as at a time of day, hourly, weekly, monthly yearly, or using another calendar-based time frame. The profile can include a summary of an individual or plurality of individuals' mental state analysis.

The flow 100 further comprises categorizing the individual with others from the plurality of people 150 based on the correlating. A personal emotional profile can be categorically classified alongside other individuals' emotional profiles. The classification can comprise placing the individual's profile in category to show a relationship between individuals based upon their emotional profile. The categorizing can include evaluation of facial expressions for anger, sadness, happiness, or disgust. The classification of individuals with related emotional profiles can be used to systematize and label an individual's emotional profile. For example, an individual's profile can be classified in an expressive category or a non-expressive category. Continuing, an individual's profile can be classified in a melancholy category or an anxious category along with profiles from other individuals exhibiting similar characteristic markers of anxiety or melancholy. Categories for classifying different emotional associations can be defined between complementary associations of emotional characteristics, such as sadness, contentedness, worry, excited, calm, happiness, fear, anxiety, and others. Categories can include expected responses to stimuli. For example, individuals could be categorized based on reactions to particular film types such as romantic films or action films. Categories and analysis can be included in charts, tables, and maps used to describe current, past, and/or future characteristics of a particular emotional profile. The categorization of emotional profiles can also be used to define types for both individuals and groups of individuals, including but not limited to demographic groups of individuals. A group's profile can be classified in a similar manner to an individual's profile, either by using emotional categories such as grouping by similar expressiveness measurements, or by using categories based on other criteria such as shared enjoyment of a particular movie genre. The flow 100 can include making a recommendation for digital media based on the categorizing. The flow can include pushing media content to the individual based on the categorizing. The digital media can include one or more of a movie, a television show, a web series, a webisode, a video, a video clip, an electronic game, an e-book, an e-magazine, or another media presentation. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
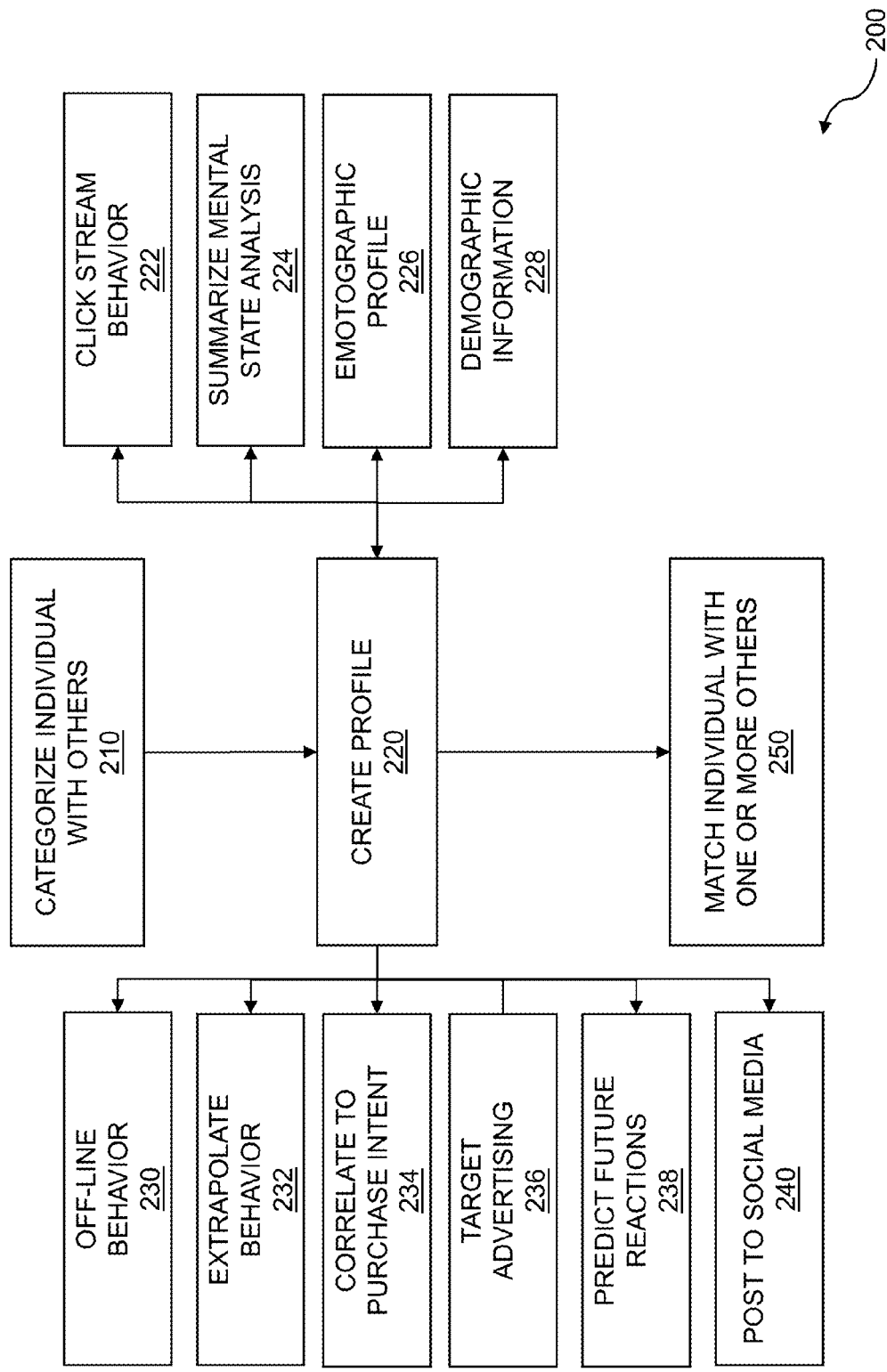
FIG. 2 is a flow diagram for personal emotional profile usage.

FIG. 2 is a flow diagram for personal emotional profile usage. The flow 200 can continue from or be part of the previous flow 100. The flow 200 can include having an individual's emotional profile placed in a category along with other individuals' emotional profiles 210. The categorizing can comprise matching the individual with one or more people from a plurality of people, based upon how both the individual and the one or more other people are categorized. The categorization can also be used to define types for both individuals and groups of individuals, including but not limited to demographic groups of individuals as set out in the description for FIG. 1. The categorization of an individual or a group of individuals can be used create an individual's personal emotional profile 220.

The emotional profile of an individual can comprise a click stream behavior 222. A clickstream is a recording of the parts of the screen a computer user clicks on while web browsing or using another software application. As the user clicks anywhere in the webpage or application, the action is logged. The clickstream behavior 222 of an individual or plurality of individuals can be used to group the individual or the plurality of individuals into a category. The profile of an individual can further be correlated with the profiles of a plurality of individuals to predict clickstream behavior for the individual. The analysis can be used to modify a web page or application based on the emotional profile created by using clickstream data.

Personal emotional profile information can also be used to create a summary based upon an analysis of an individual's mental state 224. A summary can include a user's personal emotional state, a category for an emotional profile, demographic and other statistical information, and other criteria such as perceptions, sensations, dreams and daydreams, moments of despair, boredom, flashes of inspiration, recollections, images seen in the mind's eye, thoughts, and many others. This summary can be compared to and correlated with the summary emotional profile information from other individuals in order to include the individual in a previously defined category.

The profile can comprise an emotographic profile 226. The emotographic profile can include emotional data, statistics, and categories of emotions that can be used to characterize, label, or type an individual or plurality of individuals. The emotographic profile of an individual can include information about the individual's adherence to, or deviation from, the norms of a plurality of individuals. The emotographic profile of an individual can include a category of similarly situated individuals. The profile can also include demographic information 228. Additionally, personal emotional profile information can also be used to further define or augment demographic information of an individual or plurality of individuals 228. The demographic characteristics used to classify the individual and/or the group can include any demographic including but not limited to age, sex, marital status, literacy/education, employment status and occupation, geographical location, place of birth, language, religion, nationality, ethnicity, race, and citizenship. In some embodiments individuals who comprise a group defined by one or more demographic attributes such as those listed above will experience generally similar emotional responses to an event. A normal emotional response to a given event can be inferred based upon the aggregate response to an event or life circumstance from a plurality of members of the certain demographic group. In embodiments, demographic information is combined with emotographic profile information to categorize, label, or type an individual or plurality of individuals.

The flow 200 can include off-line behavior 230 of an individual or plurality of individuals. In embodiments, off-line behavior demonstrated by an individual is inspected by comparing the individual's off-line behavior to the off-line behavior of a plurality of individual previously analyzed to determine norms for off-line behavior. The behaviors can be correlated to form a category. An individual can be categorized based upon their adherence to, or deviation from, the expected responses for a given category. The flow 200 can further comprise extrapolating behavior 232. The future behavior of an individual can be predicted based upon the correlation of the individual to other individuals in a similar circumstance. For example, individuals whose emotional profile has been categorized as including melancholy tendencies could be predicted to enjoy long solitary walks, as a preference for long solitary walks has been extracted as a behavioral norm as among a group of individuals whose profiles include melancholic tendencies. Similarly, individuals whose emotional profile has been categorized as including delight could be predisposed to purchasing flowers. Therefore, the use of emotional profile generation can have important advantages to those interested in, for example, understanding the types of people who visit a company's website, and can aid in the correlation of an individual's intent to make a purchase 234. The flow 200 can further comprise correlating a component of the emotional profile to a purchase intent 234. Certain emotional profiles can represent individuals predisposed to impulse purchases while other emotional profiles can correspond to individuals who purchase based on extensive research. Certain emotional profiles can be correlated to individuals with a greater affinity to the purchase of certain products or services.

The flow 200 can include targeting advertisements 236 based on the profile. Emotional profile generation can give advantages to those interested in assessing the effectiveness of advertising, and, in embodiments, can help advertisers appropriately target advertising 236 to an individual or plurality of individuals. An advertisement can be shown to an individual because the individual previously evidenced a positive emotional profile state in response to certain similar advertisements. In some embodiments, an advertisement that correlates to the emotional profile of an individual based upon a period of time, time of day, or another calendar time frame is shown to an individual. Advertisement timing can be chosen based upon the emotional profile status of an individual. For example, by picking the correct time point for an advertisement to be shown based upon the profile status of an individual, viewers can be retained through commercial breaks in a program. Various types of mental state information can be used to automatically determine advertisement placement, such as excitement, interest, or other emotional profile information. In other embodiments, the advertisements are offered in different locations, with emotional profile data collected in order to determine which advertisement placement generates the most desirable emotional status. The response to an advertisement by an individual can be correlated with the response to the advertisement by a plurality of people to categorize the profiles of the group. The profile of an individual can be refined based upon their adherence to, or deviation from, the norms established for the category.

Thus emotional profile generation could aid business marketers, among others, in predicting an individual's willingness to make a purchase or might infer a predicted response to an advertisement. Personal emotional profiles can also be used to predict future reactions 238 to many other events or life circumstances including prediction of future reactions to stimuli 238. Emotional profiles can be used to improve the accuracy of emotional forecasts for events or life circumstances. Also, emotional profiles generated to include demographic, emotographic, or other group associations can be used to predict the future reactions of a group to similar events or similar life circumstances. The response to an event or life circumstance by an individual can be correlated with the response to the event or life circumstance by a plurality of people to categorize the profiles of the group. The profile of an individual can be refined based upon their adherence to, or deviation from, the norms established for the category. The flow 200 can include using the profile to predict a preference.

The flow 200 can further comprise posting a representation of the profile to a social media site 240. In various embodiments, the rendering can be graphical, pictorial, textual, auditory, or any combination thereof. In some embodiments, the emotional profile is represented by an avatar. The avatar can be selected by the individual. The avatar can be animated based on the emotional profile information. For example, if the individual is excited, the avatar may change to an appearance suggesting excitation.

The flow 200 can further comprise matching the individual emotional profile with one or more profiles from a plurality of other people 250, based on the categorizing. For example, the emotional profile could be used to match entrepreneurs with different but compatible skills in technology startups, or match potentially compatible couples on web dating sites. By matching the emotional responses of individuals with the emotions of a plurality of individuals, norms for a group, including a demographic group, can be analyzed. By analyzing the response differences of an individual from the norms established for the group, an individual profile can be refined. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
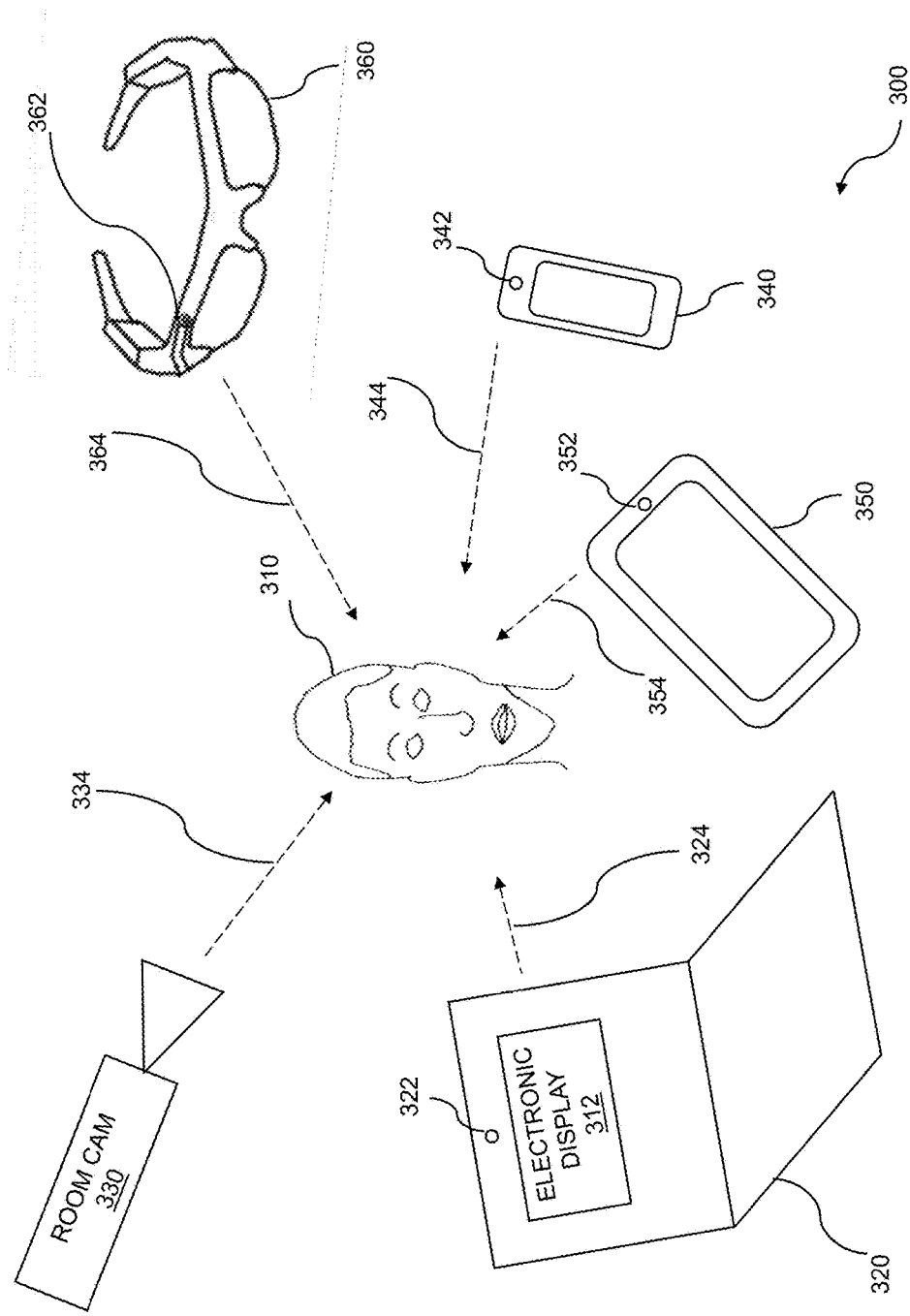
FIG. 3 is diagram showing various collection of facial mental-state data.

FIG. 3 is an example diagram showing various collection of facial mental state data. The collection of the facial mental state data is used to generate a personal emotional profile. A user 310 could be performing a task, such as viewing a media presentation on an electronic display 312 or doing another task where it can prove useful to determine the user's mental state. The mental state data can be collected while the individual views a collection of digital media. The mental state data from a plurality of people can be based on the plurality of people viewing digital media. The digital media can include one or more of a movie, a television show, a web series, a webisode, a video, a video clip, an electronic game, an e-book, or an e-magazine.

The electronic display 312 can be on a laptop computer 320 as shown, a tablet computer 350, a cell phone 340, a desktop computer monitor, a television, or any other type of electronic device. The mental state data can be collected on a mobile device such as a cell phone 340, a tablet computer 350, or a laptop computer 320 and can be collected through a biosensor, in embodiments a wearable biosensor. Thus, the multiple sources may include a mobile device, such as a phone 340, a tablet 350, or a wearable device such as glasses 360 or an attached biosensor. A mobile device can include a forward facing camera and/or a rear facing camera that can be used to collect mental state data. Facial data can be collected from one or more of a webcam 322, a phone camera 342, a tablet camera 352, a wearable camera 362, and a room camera 330. The analyzing of the mental state data can be accomplished, at least in part, on a device doing the collecting of the mental state data.

As the user 310 is monitored, the user 310 might move due to the nature of the task, boredom, distractions, or for another reason. As the user moves, the user's face can be visible from one or more of the multiple sources. Thus, if the user 310 is looking in a first direction, the line of sight 324 from the webcam 322 might be able to observe the individual's face, but if the user is looking in a second direction, the line of sight 334 from the room camera 330 might be able to observe the individual's face. Further, if the user is looking in a third direction, the line of sight 344 from the phone camera 342 might be able to observe the individual's face. If the user is looking in a fourth direction, the line of sight 354 from the tablet camera 352 might be able to observe the individual's face. If the user is looking in a fifth direction, the line of sight 364 from the wearable camera 362 might be able to observe the individual's face. A wearable device such as the pair of glasses 360 shown can either be worn by another user or an observer. In other embodiments, the wearable device is a device other than glasses, such as an earpiece with a camera, a helmet or hat with a camera, a clip-on camera attached to clothing, or any other type of wearable device with a camera or another sensor for collecting mental state data. The individual 310 can also wear a device including a camera which can be used for gathering contextual information and/or collecting mental state data on other users. Because the individual 310 can move his or her head, the facial data can be collected intermittently when the individual is looking in a direction of a camera. At times and in certain embodiments, multiple cameras are able to observe a single person. In some cases, multiple people can be included in the view from one or more cameras, and some embodiments include filtering out faces of one or more other people to determine whether the individual 310 is looking towards a camera.

Figure 4:
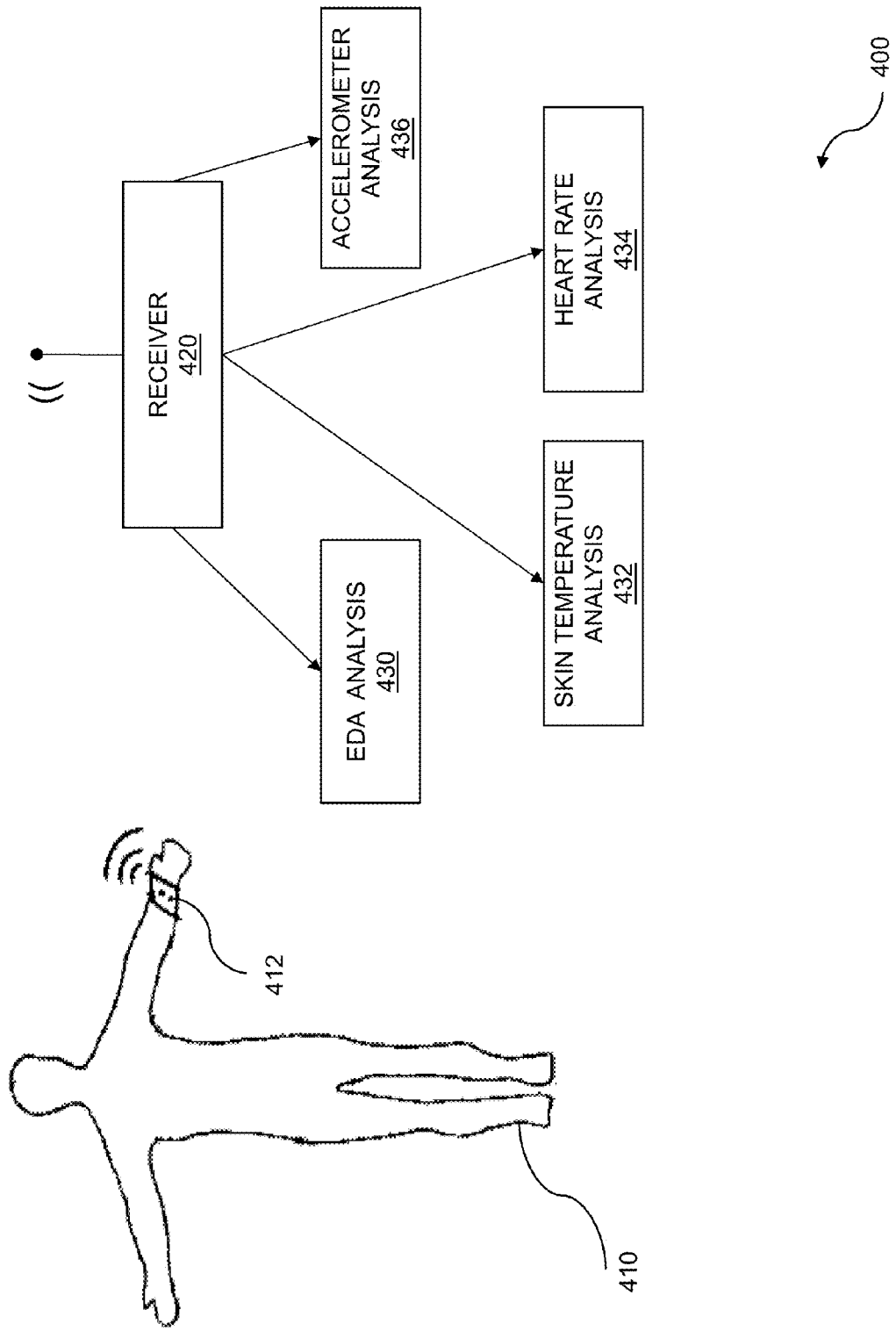
FIG. 4 is an example biosensor on a person.

FIG. 4 is an example of a biosensor on a person where biosensor information can be used in the generation of an emotional profile. A diagram 400 shows various ways a biosensor could provide data useful in creating the personal emotional profile of an individual. Physiological data can be gathered from a person 410 to determine their emotional state. A physiological monitoring device 412 can be attached to a person 410. The monitoring device 412 can be used to capture a variety of types of physiological data from a person 410 as the person experiences and interacts with various stimuli. The physiological data can include one or more of heart rate, heart rate variability, blink rate, electrodermal activity, skin temperature, respiration, accelerometer data, and the like. The physiological data can be derived from a biosensor. In embodiments, a plurality of people can be monitored as they view and interact with various stimuli.

A person 410 can experience and interact with various stimuli in a variety of ways. Physiological data collected from a person 410 as he or she interacts with various stimuli can be transmitted wirelessly to a receiver 420. In embodiments, physiological data from a plurality of people is transmitted to a receiver 420 or to a plurality of receivers. Wireless transmission can be accomplished by a variety of techniques including, but not limited to, IR, Wi-Fi, Bluetooth, and the like. In embodiments, the physiological data can be sent from a person to a receiver via tethered or wired methods. Various types of analysis can be performed on the physiological data gathered from a person or a plurality of people in order to determine their emotional profile. For example, electrodermal activity (EDA) 430 data can be analyzed to identify specific characteristics of an individual's emotional state. The electrodermal activity data can also be analyzed to determine a specific activity's peak duration, peak magnitude, onset rate, delay rate, and the like.

Additional types of analysis can be performed on the physiological data gathered from a person or a plurality of people to determine the people's collective or individual emotional profiles. For example, skin-temperature analysis 432 can be performed to measure skin temperature, temperature change rate, temperature trending, and the like. Heart-rate analysis 434 can also be performed. Heart-rate analysis can include determining heart rate, changes in heart rate, and the like. Further analysis of physiological data can include accelerometer analysis 436. Accelerometer data analysis can include determining activity, rate of activity, and the like. In embodiments, other types of analysis are performed on physiological data gathered from a person or a plurality of people to determine the emotional profile of an individual or a plurality of individuals.

Figure 5:
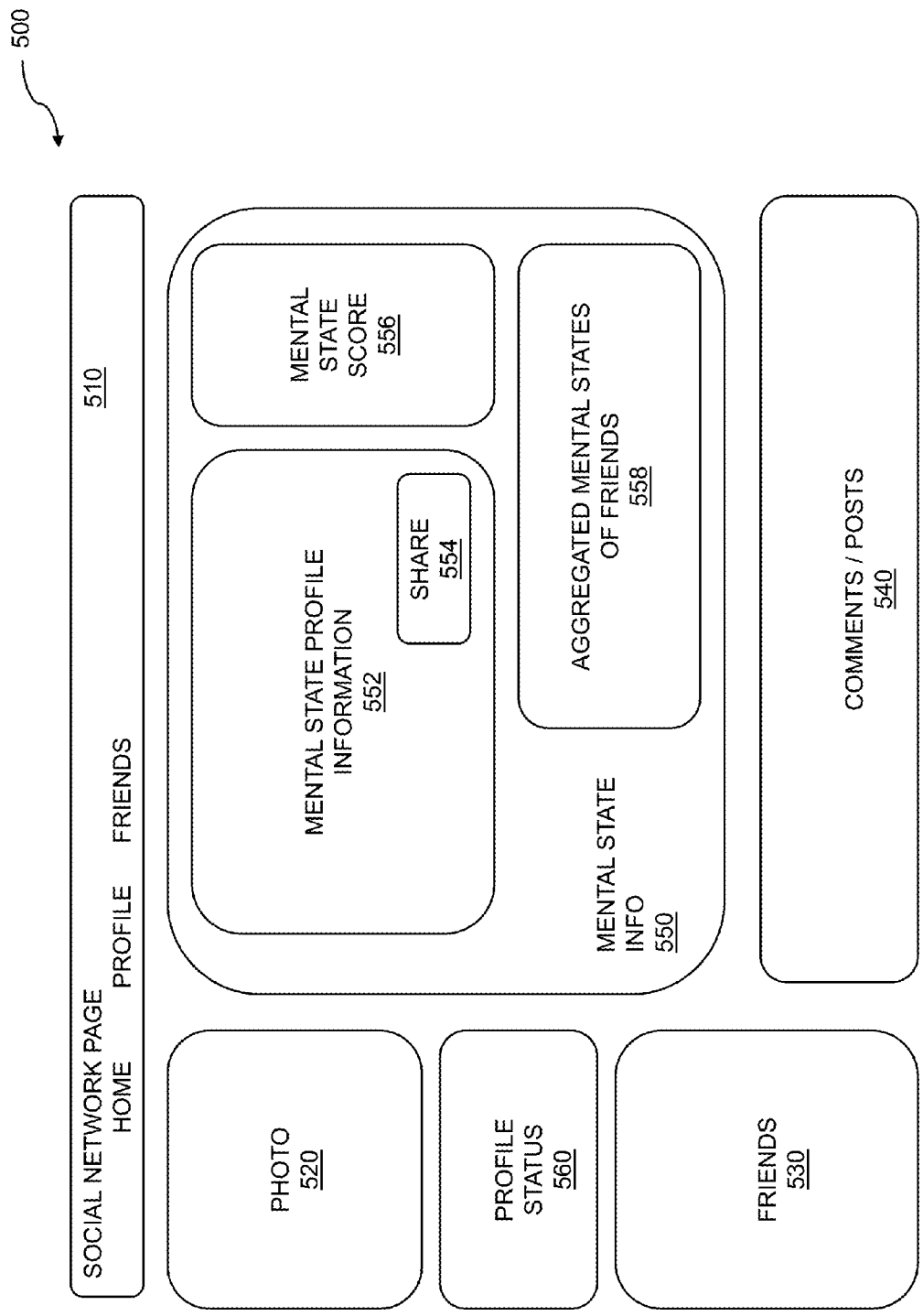
FIG. 5 is an example social network page with profile information.

FIG. 5 is an example social network page with information on emotional profiles. The example page can include posting a representation of the profile to a social media site. The exact content and formatting can vary between various social networks, but similar content can be formatted for a variety of social networks including, but not limited to, various number of blogging websites, Facebook™, LinkedIn™, MySpace™, Twitter™, Google+™, or other social network. A social network page for a particular social network can include one or more of the components shown in the example social network page content 500, but can also include various other components in place of, or in addition to, the components shown. The social network content 500 as shown in the example can include a header 510 to identify the social network and can include various tabs or buttons for navigating the social network site, such as the "Home," "Profile," and "Friends" tabs shown. The social network content 500 can also include a profile photo 520 showing the individual that owns the social network content 500. Various embodiments also include a friends list 530 showing the contacts of the individual on the particular social network. Some embodiments include a comments/posts component 540 to show posts and various comments from the individual, friends, or other parties.

The social network content 500 can include the emotional profile status of the individual 560. In various embodiments, the rendering can be graphical, pictorial, textual, auditory, or any combination thereof. In some embodiments, an avatar can be used to communicate emotional profile information.

The social network content 500 can include a mental state information section 550. The mental state information section 550 can allow for posting mental state information to a social network page. The posted mental state information can include mental state information that has been shared by the individual or can include mental state information that has been captured but not yet shared, depending on the embodiment. In at least one embodiment, a mental state graph 552 is be displayed to the individual showing the individual's own mental state information while viewing a web-enabled application. If this mental state information has not yet been shared over the social network, a share button 554 can be included. If the individual clicks on the share button 554, mental state profile information 552, such as a mental state graph or emoticon, or various summaries of the mental state information, can be shared over the social network. The mental state information can be shared with another individual, a group or subgroup of contacts or friends, another group defined by the social network, or openly with anyone, depending on the embodiment and the individual's selection. The profile photo 520, or another image shown on the social network, can be updated with an image of the individual demonstrating in some manner the mental state information that is being shared, such as a smiling picture if the mental state information indicates happiness. In some cases, the image of the individual is taken during a peak time of mental state activity. In some embodiments, the photo 520 section or some other section of the social network page 500 allows for posting video of the individual's reaction or representing the individual's mental state information along with the photo. If the mental state information shared is related to a web-enabled application, forwarding a reference to the web-enabled application as a part of the sharing of the mental state information can be performed and can include a URL and a timestamp indicating a specific point in a video. Other embodiments include an image of material from the web-enabled application or a video of material from the web-enabled application. The forwarding, or sharing, of the various mental state information and related items can be accomplished on a single social network, or some items can be forwarded on one social network while other items are forwarded on another social network. In some embodiments, the sharing is part of a rating system for the web-enabled application, such as aggregating mental state information from a plurality of users to automatically generate a rating for videos.

Some embodiments include a mental state score 556. In some embodiments, the mental state data is collected over a period of time and the mental state information that is shared is a reflection of a mood for the individual and is displayed in the form of a mental state score 556. The mental state score can be a number, a sliding scale, a colored scale, various icons or images representing moods, or any other type of representation. Various moods can be represented, including, but not limited to, frustration, confusion, disappointment, hesitation, cognitive overload, focusing, being engaged, attending, boredom, exploration, confidence, trust, delight, and satisfaction. Some embodiments include a section for aggregated mental states of friends 558. This section can include an aggregated mood of those friends shown in the friends section 530 who have opted to share their mental state information. In some embodiments, the social network page can have an interface for querying well-being statuses across the social network. The query can be directed towards people to whom an individual is linked, to friends, to a demographic group, or to some other grouping of people. Embodiments can include aggregated mental states of those friends who have viewed the same web-enabled application as the individual, thus allowing the individual to compare their mental state information in the mental state profile information 552 to their friends' aggregated mental state information 558. Other embodiments display various aggregations from different groups.

Figure 6:
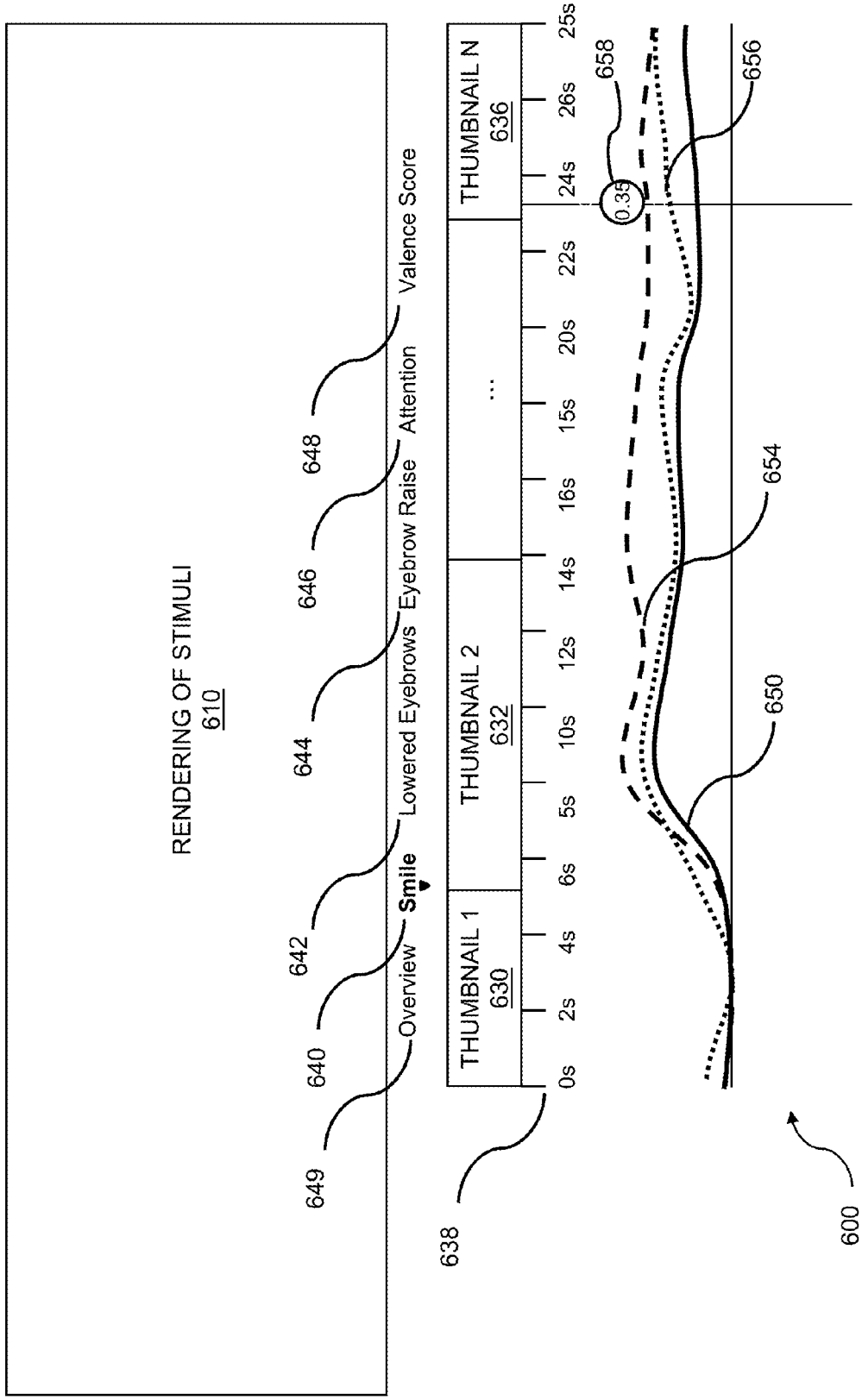
FIG. 6 is an example rendering of personal emotional analysis.

FIG. 6 is an example showing a rendering of personal emotional analysis. Such rendered analysis can be useful in generating an emotional profile or displaying the results of an emotional profiling effort. The rendering 600 can be shown on any type of display including, but not limited to, a television monitor, a projector, a computer monitor (including a laptop screen, a tablet screen, a net book screen, and the like), a cell phone display, a mobile device, or another electronic display. A rendering of stimuli 610 can be presented in the display. The example rendering 600 shown includes the rendered stimuli 610 along with associated mental state information. In some embodiments, a user can select among a plurality of stimuli. A list box or drop-down menu can be used to present a list of various stimuli for display. The user interface can allow a plurality of parameters to be displayed as a function of time, synchronized to the stimuli. Various embodiments can have any number of selections available for the user, with some being other types of renderings instead of video, including audio, text, still images, or other kinds of media. A set of thumbnail images for the selected rendering—in the example shown, the thumbnails include Thumbnail 1 630 and Thumbnail 2 632 through Thumbnail N 636—can be shown below the rendering along with a timeline 638. The thumbnails can show a graphic "storyboard" of the stimuli rendering 610. In some embodiments, one or more of the thumbnails are vignettes that include motion. The storyboard can assist a user in identifying a particular scene or location within the media presentation 610. Some embodiments do not include thumbnails, or have a single thumbnail associated with the stimuli presentation 610. Other embodiments have thumbnails of equal length while still others have thumbnails of differing lengths. In some embodiments, the start and/or end of the thumbnails is determined based on changes in the captured viewer mental states associated with the rendering, or is based on particular points of interest in the stimuli presentation 610. Thumbnails showing the one or more viewers can be shown in addition to, or in place of, the media-presentation thumbnails, such as thumbnail 1 630 and thumbnail 2 632 through thumbnail N 636, along the timeline 638. The thumbnails showing viewers can include peak expressions, expressions at key points in the stimuli, and the like.

Some embodiments include the ability for a user to select a particular type of mental state information for display using various buttons or other selection methods. For example, in the rendering 600 shown, the user has previously selected the Smile button 640, because smile mental state information is displayed. Other types of mental state information available for user selection in various embodiments include the Lowered Eyebrows button 642, Eyebrow Raise button 644, Attention button 646, Valence Score button 648, or other types of mental state information, depending on the embodiment. In embodiments, an Overview button 649, which allows a user to display graphs of the multiple types of available mental state information simultaneously, is available. The rendering 600 may include inferred mental states about the stimulus based on the mental state data which was collected. The mental states can include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The mental state information can include probability information for one or more effectiveness descriptors and the probabilities for the one of the one or more effectiveness descriptors can vary for portions of the advertisement.

Because the Smile option 640 has been selected in the example shown, smile graphs are displayed. In this example, a male smile graph 650 and a female smile graph 654 are shown, with the aggregated mental state information displayed visually. Another collective graph 656 for smiles by a different subset of people can be shown as well. The mental state information can be based on various demographic groups as they react to given stimuli. The various demographic-based graphs can be visually differentiated using various line types as shown in FIG. 6, or can be indicated using color or another method of differentiation. In embodiments, a slider is included to allow a user to select a particular time on the timeline and show the value of the chosen mental state for that particular time. The slider can be rendered using the same line type or color as the demographic group whose mental state information is under analysis. A value 658 can be included with the slider to indicate a numeric representation of a specific value for the mental state of a chosen demographic at a particular time, or the value can be included to numerically display another useful measurement.

A user might be interested in evaluating the mental state of a particular demographic group, such as people of a certain age range or gender. In some embodiments, the mental state data is compared with self-report data collected from a group of viewers. In this way, the analyzed mental states can be compared with the self-report information to see how well the two data sets correlate. The rendered analysis 600 can be used to optimize the emotional profile. In some cases, different versions of the stimuli are available by using selection buttons. Further, there can be additional buttons for selection which allow for different types of optimization of the stimuli presentation.

Figure 7:
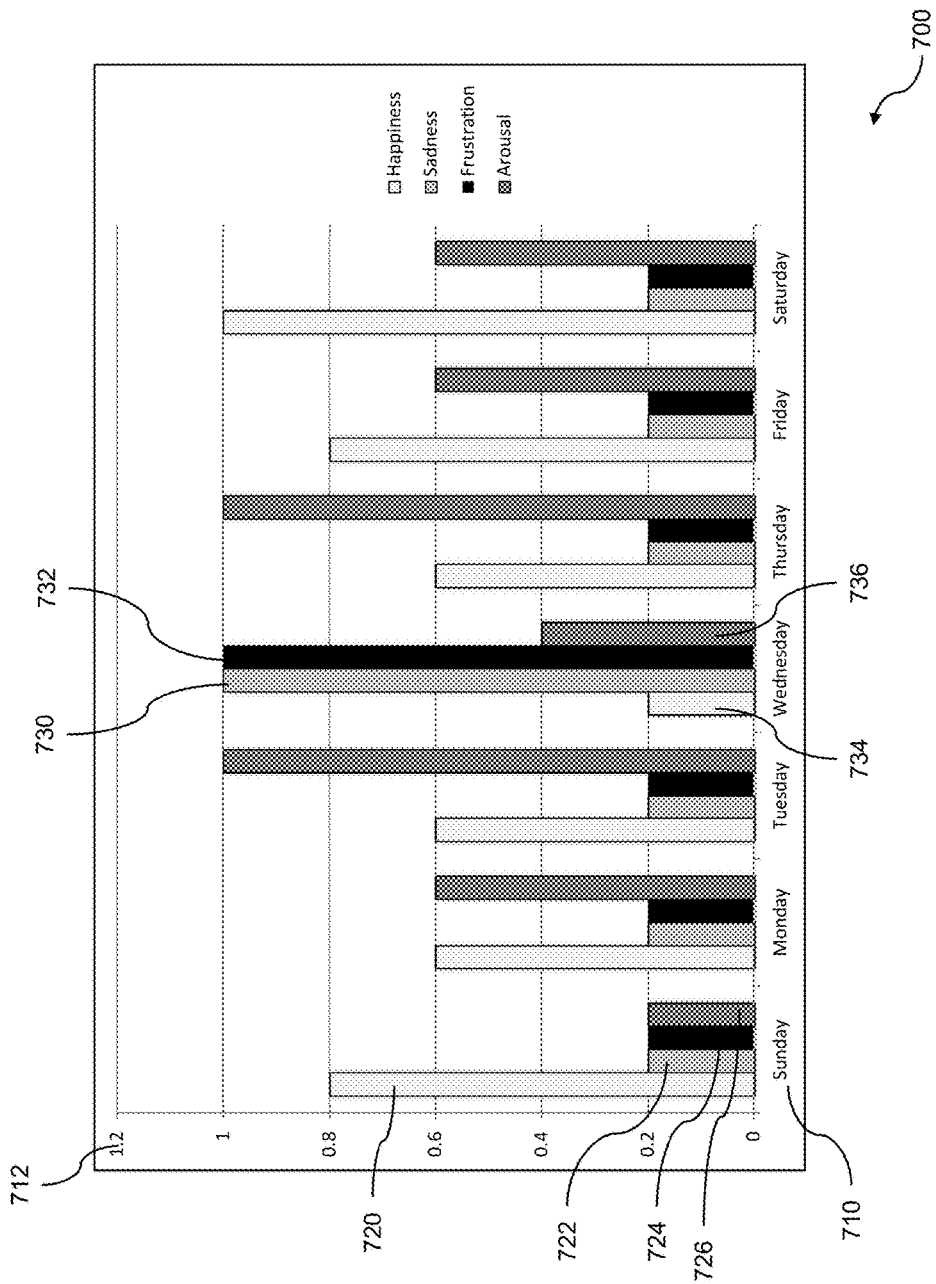
FIG. 7 is an example bar graph with mental states.

FIG. 7 is an example bar graph with mental states across a period time. Such a graphing of mental states can aid in visualizing an emotional profile, aspects of an emotional profile, the results of an emotional profiling effort, and so on. The graph 700 can be presented on any type of a display appropriate to displaying such data, including, but not limited to, a television monitor, a projector, a computer monitor (including a laptop screen, a tablet screen, a net book screen, and the like), a cell phone display, a mobile device, or another electronic display, or the graph can be printed. The graph can include one or more mental state parameters based on mental state information. The example graph 700 shows a weekly calendar 710 from Sunday through Saturday but displaying across any period of time could be useful including a day, a month, a year, or another period. In the example graph 700, mental state parameters are shown including happiness 720, sadness 722, frustration 724, and arousal 726. Any number of mental state parameters appropriate to mental state analysis can be graphed. The graph can be generated to show one or more mental state parameters for a specific time period. Similarly, the graph can display a scale 712 appropriate to the various parameters, such as a range of values between zero and one. Any units, scale, or range of values appropriate to the given parameters can be graphed.

The mental state parameters in a graph can be analyzed for various purposes including to identify trends, consistency, abrupt changes, and so on. The amount of mental state parameter value change that signals an abrupt change can be chosen from a value, range of values, and so on. Graph 700 illustrates some abrupt changes in the example parameters for the day Wednesday. While graphed information in the example shows relative consistency in the values of the various parameters along with some positive or negative trends for the week, the example mental state parameter values for Wednesday are markedly different. In the example shown, the parameter happiness has a value of 0.8 on Sunday 720 but only a value of 0.2 on Wednesday 734. In addition, sadness 722 and frustration 724 both have a value of 0.2 on Sunday but change abruptly on Wednesday to values of 1.0 for sadness 730 and 1.0 for frustration 732. Finally, the parameter arousal has a value of 0.2 on Sunday 726 and a value of 0.4 on Wednesday 736. Identification of abrupt changes in the various mental state parameters which are presented in a graph can be useful for a variety of purposes including studying an individual, a plurality of individuals, a demographic group such as people of a certain age range or gender, and so on. In some cases, an emotional profile is generated for an individual or group of people where a trend for mental states can be anticipated through the week. After predicting the trend the profile could be used to suggest activities. Deviations from the profile, such as an elevation in sadness and frustration, could be used to alter recommendations. In some cases the recommendations could include exercising, watching a movie, visiting a counselor, or other activities.

The mental state parameters in a graph can be dependent on or independent of each other. For example, happiness 720 can inversely depend on or inversely track with sadness 722. Similarly, happiness might not be dependent upon nor track with another parameter. For example, happiness 720 might not depend on nor track with arousal. The graph can be analyzed to identify interdependencies between and among various mental state parameters or other parameters. For example, an increase in one parameter may correlate with a rise or a fall in another parameter.

Figure 8:
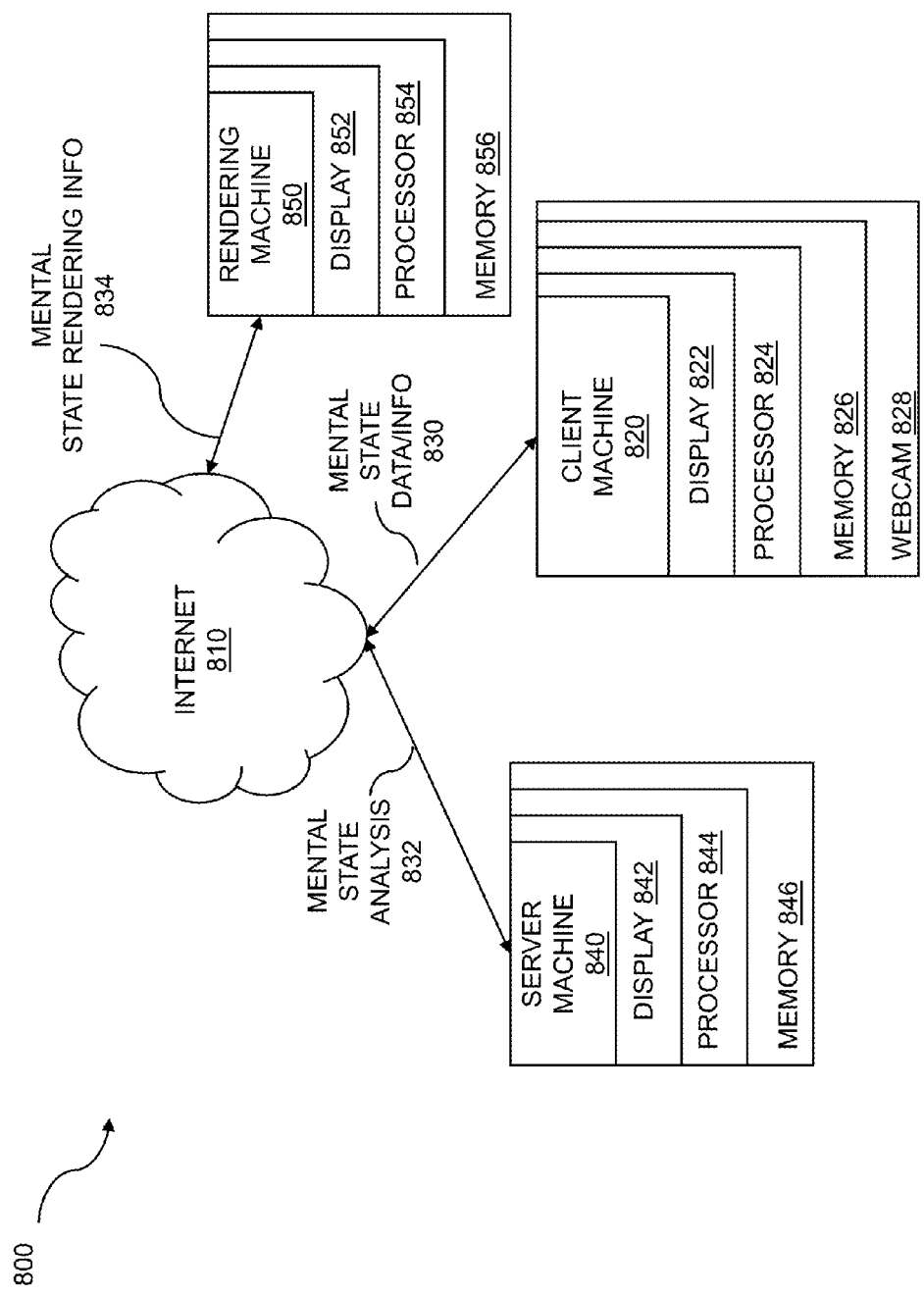
FIG. 8 is a system for personal emotional profile usage.

FIG. 8 is a system diagram for personal emotional profile generation and usage. The system 800 can perform a computer-implemented method for mental state analysis comprising receiving mental state information on an individual, analyzing the mental state data to evaluate a mental state status for the individual, correlating the mental state information of the individual with mental state information from a plurality of people, categorizing the individual with others from the plurality of people based on the correlating, and sending a result of the categorizing for rendering.

The system 800 can include one or more client machines 820 linked to an analysis server 840 via the Internet 810 or another computer network. The client machine 820 can include one or more processors 824 coupled to a memory 826 which can store and retrieve instructions, a display 822, and a webcam 828. The display 822 can be any electronic display, including but not limited to a computer display, a laptop screen, a net-book screen, a tablet computer screen, a cell phone display, a mobile device display, a remote with a display, a television, a projector, or the like. The webcam 828 can comprise a video camera, a still camera, a thermal imager, a CCD device, a phone camera, a three-dimensional camera, a depth camera, multiple webcams used to show different views of a person, or any other type of image capture apparatus that allows captured data to be used in an electronic system. In embodiments, the analysis server 840 includes one or more processors 844 coupled to a memory 846 which can store and retrieve instructions, and can also include a display 842.

In some embodiments, the rendering of emotional status can occur on a different computer than the client machine 820 or the analysis server 840. This computer can include a rendering machine 850 which can receive mental state analysis 832 from the analysis machine 840, mental state data 830 from the client machine 820, or both. The data received by the rendering machine 850 can be considered mental state rendering information 834. In embodiments, the rendering machine 850 includes one or more processors 854 coupled to a memory 856 which can store and retrieve instructions, and can include a display 852.

The analysis server 840 can receive the mental state data and analyze the mental state data to produce emotional status information, so that the analyzing of the mental state data can be performed by a web service. The analysis server 840 can use the mental state information received from the client machine 820 or produced from the mental state data to analyze an individual's emotional profile. In some embodiments, the analysis server 840 receives mental state data and/or mental state information from a plurality of client machines, and aggregates the mental state information for use in optimizing the emotional status of an individual or plurality of individuals. In at least one embodiment, the client machine, analysis server, and/or rendering functions can be accomplished by one computer.

The system 800 can further perform a computer-implemented method for mental state analysis including collecting mental state data from an individual, analyzing the mental state data to produce mental state information, and sending the mental state information to a server wherein the server can correlate the mental state information of the individual with mental state information from a plurality of people and categorize the individual with others from the plurality of people based on the correlating. The system 800 can perform a computer-implemented method for mental state analysis comprising receiving a categorization for an individual with others from a plurality of people based on correlation of mental state information where the mental state information resulted from analyzing mental state data captured from the individual, and rendering an output based on the categorization which was received. The system 800 can further include a computer program product embodied in a non-transitory computer readable medium for mental state analysis comprising code for collecting mental state data from an individual, code for analyzing the mental state data to produce mental state information, code for correlating the mental state information of the individual with mental state information from a plurality of people, and code for categorizing the individual with others from the plurality of people based on the correlating.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"— may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
   obtaining mental state data from an individual, wherein the mental state data is extracted, using one or more processors, from facial images of an individual captured as they respond to stimuli;
   analyzing the mental state data extracted from facial images to produce mental state information;
   correlating the mental state information of the individual with mental state information from a plurality of people, wherein the mental state information from the plurality of people is determined as a function of at least one historical environmental condition measured from ambient conditions affecting at least one of the plurality of people and stored as historical contextual information;
   categorizing, using one or more processors, the individual with others from the plurality of people based on the correlating and a rate of change of a plurality of expressions of the individual, wherein the rate of change is evaluated during exposure to specific stimuli and wherein the categorizing is part of a profile;
   determining at least one recent environmental condition by measuring an ambient condition affecting the individual during the exposure to specific stimuli and storing the measurement as recent contextual information; and predicting a future reaction to a stimulus, based on the profile, the historical contextual information, and the recent contextual information.

2. The method of claim 1 wherein the profile summarizes mental state analysis.

3. The method of claim 1 wherein the profile comprises an emotographic profile of the individual.

4. The method of claim 1 wherein the categorizing includes evaluation of facial expressions for anger, sadness, happiness, or disgust.

5. The method of claim 4 further comprising pushing media content to the individual based on the categorizing.

6. The method of claim 1 wherein the profile includes demographic information.

7. The method of claim 1 further comprising extrapolating behavior based on the profile.

8. The method of claim 1 further comprising correlating a component of the profile to a purchase intent.

9. The method of claim 1 further comprising targeting advertisements based on the profile.

10. The method of claim 1 further comprising using the profile to predict a preference.

11. The method of claim 1 further comprising posting a representation of the profile to a social media site.

12. The method of claim 1 further comprising using the profile to categorize a product or service.

13. The method of claim 1 further comprising matching the individual with one or more people from the plurality of people, based on the categorizing.

14. The method of claim 1 wherein the analyzing of the mental state data is accomplished, at least in part, on a device doing collecting of the mental state data and wherein the device doing the collecting includes a mobile device.

15. The method of claim 1 wherein the obtaining is accomplished by collecting the mental state data over time.

16. The method of claim 1 wherein the obtaining is accomplished by collecting the mental state data with a plurality of devices.

17. The method of claim 1 further comprising developing norms for the individual.

18. The method of claim 17 further comprising using response differences in the individual, over an interval of time, from the norms for the individual to make a recommendation.

19. The method of claim 1 further comprising making a recommendation for digital media based on the categorizing.

20. The method of claim 1 further comprising developing norms for a demographic group.

21. The method of claim 20 further comprising using response differences for the individual from the norms for the demographic group to refine a profile.

22. The method of claim 1 further comprising performing emotional journaling based on the mental state information for the individual.

23. The method of claim 1 wherein the mental state data includes facial data, physiological data, or accelerometer data.

24. A computer program product embodied in a non-transitory computer readable medium for mental state analysis, the computer program product comprising code which causes one or more processors to perform operations of:

obtaining mental state data from an individual, wherein the mental state data is extracted from facial images of an individual captured as they respond to stimuli;

analyzing the mental state data extracted from facial images to produce mental state information;

correlating the mental state information of the individual with mental state information from a plurality of people, wherein the mental state information from the plurality of people is determined as a function of at least one historical environmental condition measured from ambient conditions affecting at least one of the plurality of people and stored as historical contextual information;

categorizing the individual with others from the plurality of people based on the correlating and a rate of change of a plurality of expressions of the individual, wherein the rate of change is evaluated during exposure to specific stimuli and wherein the categorizing is part of a profile;

determining at least one recent environmental condition by measuring an ambient condition affecting the individual during the exposure to specific stimuli and storing the measurement as recent contextual information; and predicting a future reaction to a stimulus, based on the profile, the historical contextual information, and the recent contextual information.

25. A computer system for mental state analysis comprising:

a memory which stores instructions;

one or more processors attached to the memory wherein the one or more processors, when executing the instructions which are stored, are configured to:

obtain mental state data from an individual, wherein the mental state data is extracted from facial images of an individual captured as they respond to stimuli;

analyze the mental state data extracted from facial images to produce mental state information;

correlate the mental state information of the individual with mental state information from a plurality of people, wherein the mental state information from the plurality of people is determined as a function of at least one historical environmental condition measured from ambient conditions affecting at least one of the plurality of people and stored as historical contextual information;

categorize the individual with others from the plurality of people based on the correlating and a rate of change of a plurality of expressions of the individual, wherein the rate of change is evaluated during exposure to specific stimuli and wherein the categorizing is part of a profile;

determine at least one recent environmental condition by measuring an ambient condition affecting the individual during the exposure to specific stimuli and storing the measurement as recent contextual information; and predict a future reaction to a stimulus, based on the profile, the historical contextual information, and the recent contextual information.

26. The method of claim 1 wherein the images capture physiological data.

27. The method of claim 26 further comprising extracting emotional state information from the captured physiological data.

28. The method of claim 3 further comprising periodically updating the emotographic profile of an individual as additional profile information is collected.

29. The method of claim 2 further comprising rendering, on a device of the individual, the profile and a mental state score, wherein the mental state score is based on mental state data collected over a period of time.

30. The method of claim 1 further comprising making activity recommendations based upon the profile.

31. The method of claim 30 wherein the activity recommendations are based on time of day.

32. The method of claim 30 wherein the activity recommendations are based upon a period of time during the day.

33. The method of claim 30 wherein the activity recommendations further comprise calendar date based scheduling.

34. The method of claim 1 wherein the at least one environmental condition is a temperature or humidity.

35. The method of claim 1 further comprising rendering an output comprising an emotional analysis of at least one of mental state information of the individual and mental state information from the plurality of people.

36. The method of claim 35 wherein the output comprises a graphical timeline depicting changes in the emotional state of at least one of the individual and the plurality of people.

37. The method of claim 35 wherein the output comprises a bar graph depicting relative estimated levels of at least two emotions over the course of a plurality of days.

38. The method of claim 1 wherein the analyzing includes inferring mental states.

* * * * *